United States Patent [19]
Williams et al.

[11] Patent Number: 5,490,524
[45] Date of Patent: Feb. 13, 1996

[54] SURGICAL DRAPE FOR A LASER TARGETING DEVICE USED WITH AN X-RAY MACHINE

[76] Inventors: Terry N. Williams, 2032 Thorpshire Dr., Raleigh, N.C. 27615; George R. Parrish, 815-12 Marlowe Rd., Raleigh, N.C. 27609

[21] Appl. No.: 407,332

[22] Filed: Mar. 20, 1995

[51] Int. Cl.$^6$ .......................... A61B 19/00; A61B 19/08
[52] U.S. Cl. .......................... 128/849; 128/853; 128/856
[58] Field of Search .................................... 128/849–856

[56] References Cited

U.S. PATENT DOCUMENTS

| | | | |
|---|---|---|---|
| 4,308,864 | 1/1982 | Small | 128/856 |
| 4,903,710 | 2/1990 | Jessamine | 128/852 |
| 4,905,710 | 3/1990 | Jones | 128/853 |
| 4,998,538 | 3/1991 | Charowsky | 128/856 |
| 5,127,423 | 7/1992 | Draeger | 128/854 |

Primary Examiner—Michael A. Brown
Attorney, Agent, or Firm—Rhodes, Coats & Bennett

[57] ABSTRACT

The present invention provides a surgical drape adapted to cover either end of a C-arm-type x-ray machine having a laser targeting device mounted thereon. The surgical drape is made of an x-ray-transparent material, such as plastic, and includes a transparent window made of a material that does not diffuse or diffract a laser beam, such as an acetate film. The transparent window is preferably delineated from the main, plastic sheet of the surgical drape by a colored indicator. The indicator may be, for example, a colored band surrounding the window. Alternatively, the transparent window may itself be colored. In this case, the color chosen is matched to the wavelength of the laser beam so as to allow transmission of the laser beam yet filter out other wavelengths of light. The surgical drape is preferably shaped like a bag to fit over the end of the x-ray machine's C-arm.

15 Claims, 4 Drawing Sheets

SURGICAL DRAPE FOR A LASER TARGETING DEVICE USED WITH AN X-RAY MACHINE

FIELD OF THE INVENTION

The present invention relates to sterile, disposable drapes used during surgery and particularly pertains to an x-ray-transparent surgical drape that covers a section of an x-ray machine having a laser targeting device mounted thereto and that provides a transparent window through which a targeting laser beam may pass without diffusion or diffraction.

BACKGROUND OF THE INVENTION

During surgical operations and other invasive procedures, it is conventional to cover a patient and nearby equipment with sterile drapes to prevent microorganisms and other foreign matter from invading the patient and to keep equipment clean. It has been known in the past to construct surgical drapes with cheap, easily disposable material, such as cellulosic material or plastic film. Such surgical drapes are sometimes provided with precut fenestrations to provide access to a patient with surgical tools and the like and are also sometimes provided with straps to fasten the drape to the patient or equipment.

It has also been known to construct entire surgical drapes with a transparent material to aid in viewing the patient. Such construction is shown in the patent to Jessamine et al., U.S. Pat. No. 4,903,710, which provides a surgical drape comprising a sheet of flexible transparent or translucent plastic material. It has also been known to provide a viewing window made of transparent plastic in the center of a non-transparent surgical drape. Such a viewing window is shown in the patent to Hadtke et al., U.S. Pat. No. 3,721,234, which discloses a surgical drape composed of cellulosic material with an enlarged opening and having a clear plastic sheet covering the opening.

Surgical operations and other medical procedures are often performed under an x-ray machine, which includes an x-ray emitter and an image intensifier (collector) fluoroscopy tube. Although prolonged exposure to x-rays is dangerous, medical procedures were often performed in years past using an x-ray machine that has remained on for extensive periods during the procedure so that doctors and other medical personnel could see what they were doing. Upon the advent of laser targeting devices, which aim a laser beam in the path of the x-ray beam, surgery and other operative procedures could be performed without extensive x-ray exposure. The laser beam provides a visible target that aids a doctor in maintaining an accurate reference axis without extensive operation of the x-ray machine, thereby reducing radiation exposure to doctors and patients. An example of a laser targeting device is disclosed in the inventors' co-pending U.S. patent application, Ser. No. 08/344,467, filed Nov. 23, 1994, which is hereby incorporated by reference.

One problem that has arisen with the use of laser targeting devices in surgical procedures relates to the use of a surgical drape to protect the laser targeting device and x-ray machine from blood and other contaminants inherent in surgical operations and also to prevent any microorganisms from the laser targeting device infecting the patient. Currently, laser targeting devices are generally covered with drapes made of polyethylene or other inexpensive plastic that work well to keep the devices clean, but do not permit good transmission of the laser beam through the drape. This is because drapes currently used to cover laser targeting devices are not entirely clear or are easily wrinkled and, therefore, cause diffusion and diffraction of the laser light. Another problem with previously used drapes is that such drapes are not sized and shaped specifically to cover an end of a C-arm-type x-ray machine having a laser targeting device mounted thereon. When an ordinary drape is pulled over the end of the C-arm, it generally becomes wrinkled and distorted, which enhances the aforementioned laser beam transmission problems.

SUMMARY AND OBJECTS OF THE INVENTION

The present invention provides a surgical drape that is adapted to cover a laser targeting device mounted on an x-ray machine, particularly a C-arm-type x-ray machine. To ensure optimal transmission of a laser beam through the drape, the invention provides a drape made of ordinary, inexpensive plastic, such as polyethylene, but additionally having a transparent window made of a higher quality material, such as a sheet of acetate film, which is a better transmitter of laser light than polyethylene. The acetate window does not diffuse, disperse, or diffract light as does the conventional draping material. This is both because of the acetate film's light transmitting properties and because the acetate film used in the surgical drape of the invention is flexible, yet stiff enough not to wrinkle during use.

To prevent accidental misalignment of the transparent window and to ensure that the laser beam does not pass through any part of the drape other than the transparent window, the invention provides a colored indicator that delineates the transparent window from the remainder of the drape. Two embodiments of the colored indicator are described herein. One embodiment of the colored indicator includes a colored band or ring around the transparent window to clearly indicate the window and to ensure correct positioning of the window in the path of the laser beam. The particular color used for the band or ring is a matter of choice. A second embodiment provides that the transparent window itself is made of a colored material that transmits a narrow bandwidth of light. In this case, the color chosen for the transparent window is matched to the wavelength of the laser beam to allow transmission of the laser beam through the window, yet filter out other wavelengths of light.

While the surgical drape of the present invention may be constructed with a single planar sheet material, which would be desirable with some types of x-ray machines, the surgical drape is preferably sized and shaped to fit over a laser targeting device mounted on an end of a C-arm-type x-ray machine without undue bunching or wrinkling of the drape material. This is accomplished by constructing the drape with two sheets of material that are joined by their edges into a bag-shaped drape. The transparent window is bonded into an opening in the top sheet, whereas the bottom sheet does not have any opening. The drape bag is then placed over the end of the C-arm having the laser targeting device, and tie straps attached to the drape are used to secure the drape to the x-ray machine or via bands that are included in the sterile drape pack.

Therefore, an object of the present invention is to provide a surgical drape that is designed to cover and protect a laser targeting device on an x-ray machine.

Another object of the present invention is to provide a surgical drape that permits the unimpeded transmission of a laser beam by providing a transparent window in the surgical drape that does not disperse, diffuse, or diffract the laser beam.

Another object of the present invention is to provide a surgical drape with a transparent window that has a colored indicator to delineate the transparent window from the remainder of the surgical drape.

Another object of the present invention is to provide a surgical drape having a colored transparent window that allows transmission of certain wavelengths of light.

Another object of the present invention is to provide a surgical drape formed from two sheets of material that are joined together into a bag for a proper fit over a laser targeting device mounted on one end of a C-arm-type x-ray machine.

Other objects and advantages of the present invention will become apparent and obvious from a study of the following description and the accompanying drawings, which are merely illustrative of such invention.

DETAILED DESCRIPTION OF THE INVENTION

Figure 1:
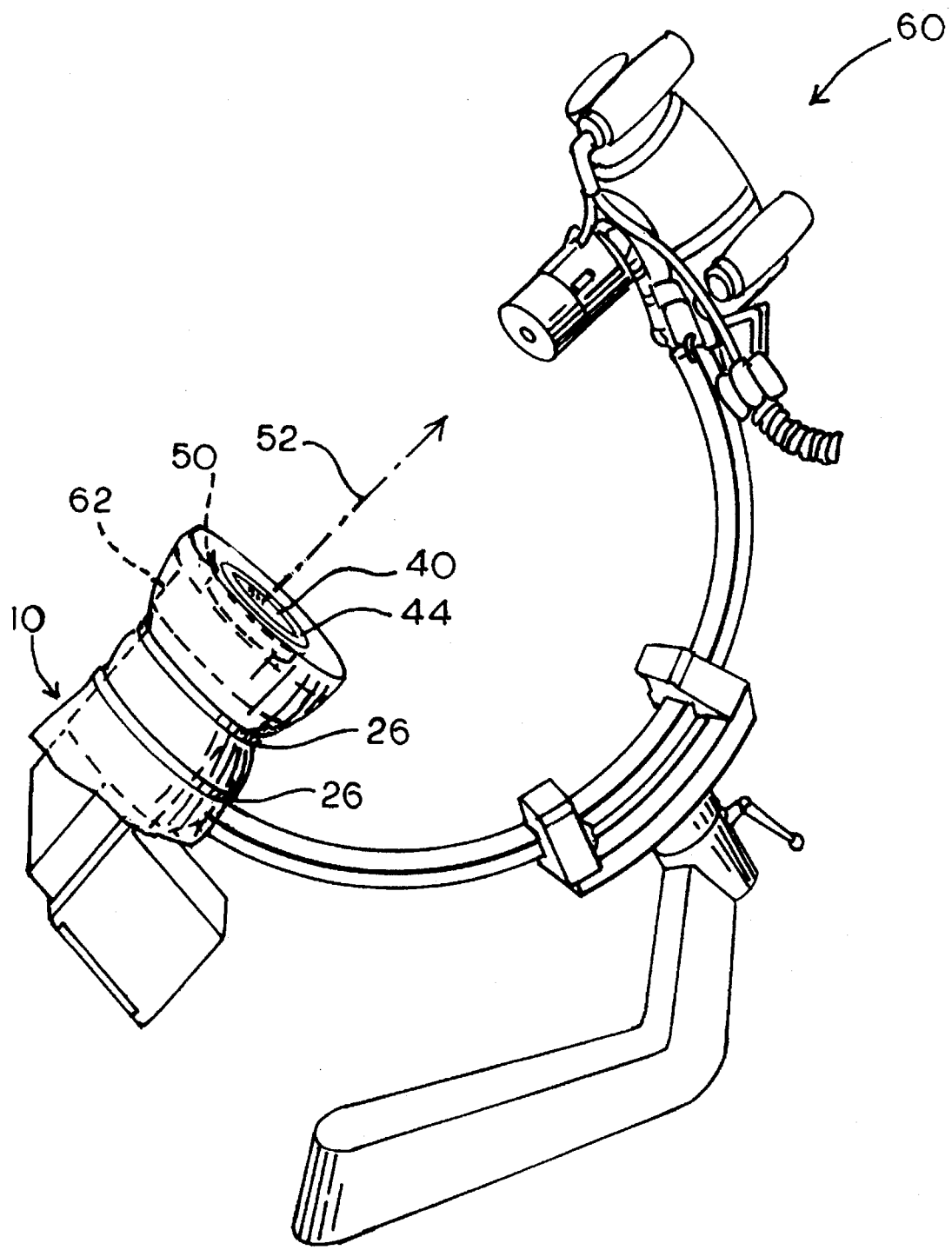
FIG. 1 is a depiction of the surgical drape of the invention covering a laser targeting device on an X-ray machine.

The present invention provides an improved surgical drape, generally indicated in the drawings by the numeral 10, that is adapted to fit over an end of a C-arm-type x-ray machine with a laser targeting device mounted thereon. In the drawings, the laser targeting device 50 is shown mounted atop the image intensifier 62 of a typical C-arm-type x-ray machine 60. It should be understood, however, that the surgical drape of the invention could be adapted for use with any type of x-ray machine having a laser targeting device mounted thereon. The surgical drape includes a transparent window, indicated by the numeral 40, which is composed of a material that allows unimpeded transmission of a laser beam 52 emitted from the laser targeting device 50 with no diffusion or diffraction.

The surgical drape 10 may be formed from a single sheet material, but as shown in the drawings, the drape 10 is preferably formed in a bag shape with a top sheet 20 and a bottom sheet 30. The top and bottom sheets 20, 30 are preferably planar and are preferably formed of a generally clear plastic, such as polyethylene, which is transparent to x-rays. Because of the inclusion of the window 40, which will be detailed later, it is not important that the sheets 20, 30 be absolutely transparent to light. In fact, in order to provide an affordable surgical drape that can be economically disposed of after a single use, the sheets 20, 30 are preferably formed from conventional, inexpensive plastic that is commonly used in surgical drapes. The primary requirement of the top and bottom sheets 20, 30 is that they be impervious to microorganisms and preferably impervious to moisture as well.

The top and bottom sheets 20, 30 are joined along their respective outer peripheries 2, 28, 32 by, for example, ultrasonic welding, heat sealing, or gluing to form a bag having an open end 34. During use, the open end 34 of the bag is pulled over the laser targeting device 50 and the image intensifier 62. Tie straps 26, which are removably attached to the top sheet 20 by an adhesive 27, are used to secure the surgical drape 10 to the x-ray machine 60 so that the drape will not be inadvertently pulled off. Rubber bands included in sterile pack can be optionally used to replace straps to enhance fit.

Figure 2:
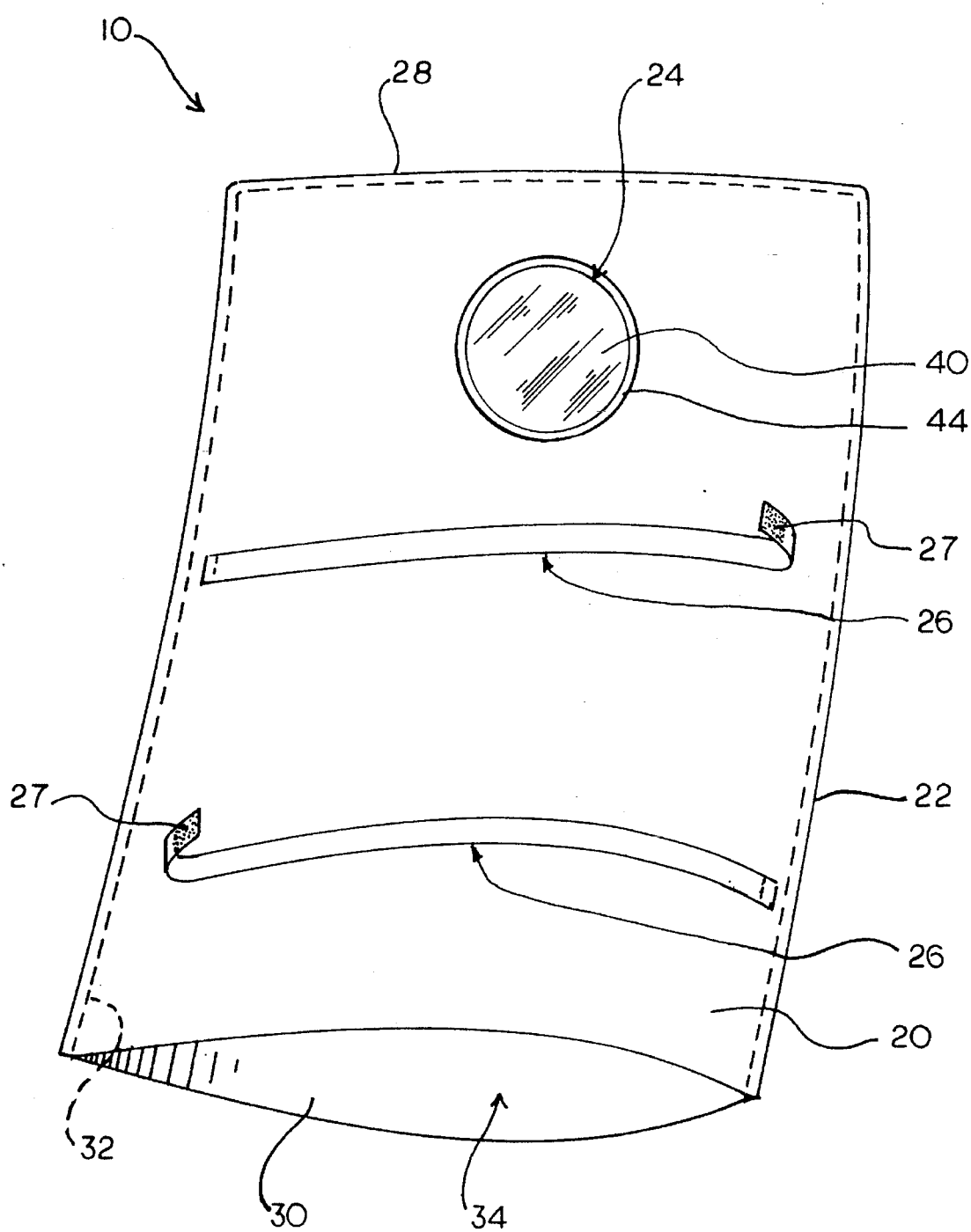
FIG. 2 shows an embodiment of the surgical drape with a colored ring surrounding the transparent window.
Figure 3:
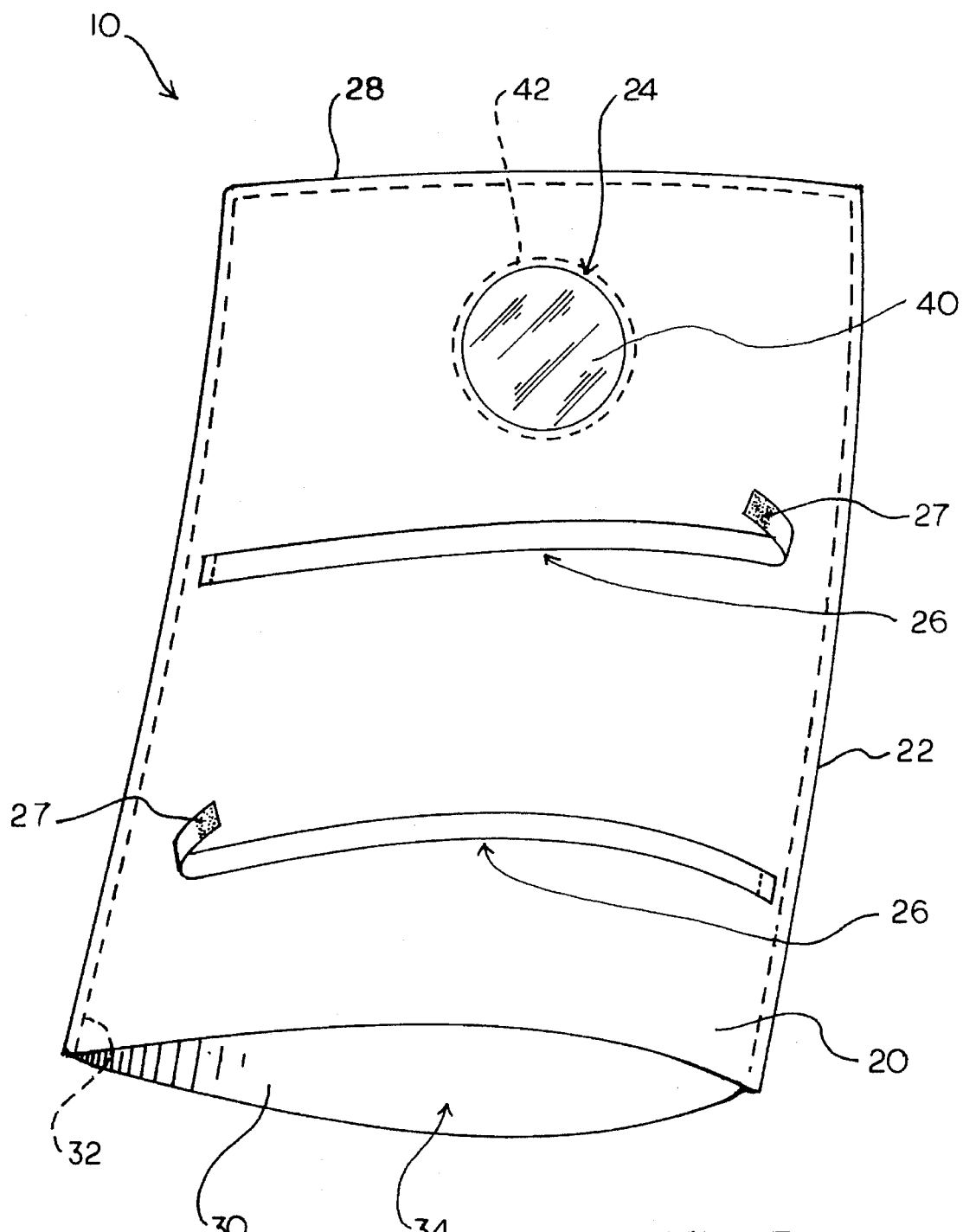
FIG. 3 shows an embodiment of the surgical drape with a colored transparent window instead of a colored ring.

The top sheet 20 includes an opening 24 inwardly of the periphery 22 of the sheet and positioned proximate the closed end 28 of the bag. The transparent window 40 is preferably mounted in the opening 24 by ultrasonic welding, heat sealing, gluing or double-sided tape so as to provide a seal around the entire periphery 42 of the window 40. In the preferred embodiment, the window 40 is round to correspond to a round top surface of a typical laser targeting device 50, such as the laser targeting device disclosed in co-pending patent application, Ser. No. 08/344,467. However, the window 40 could be any shape. In the embodiment shown in FIG. 2, a colored ring 44 is attached to the top sheet 20 and completely surrounds the window 40. The colored ring 44 may also function to help seal the joint between the periphery 42 of the window 40 and the inside edges of the opening 24 in the top sheet 20.

The transparent window 40 is composed of a planar disk of transparent material that is flexible enough to fit over varying sizes and shapes of laser targeting devices, yet is rigid enough not to wrinkle during use. The most important characteristic of the material forming the transparent window 40 is that it permit the unimpeded transmission of a laser beam without diffusion, dispersion, or diffraction of the laser beam and, of course, that it be x-ray transparent as well. While any material having these characteristics may be employed in the surgical drape 1 0, clear or colored acetate is a preferable material.

Figure 4:
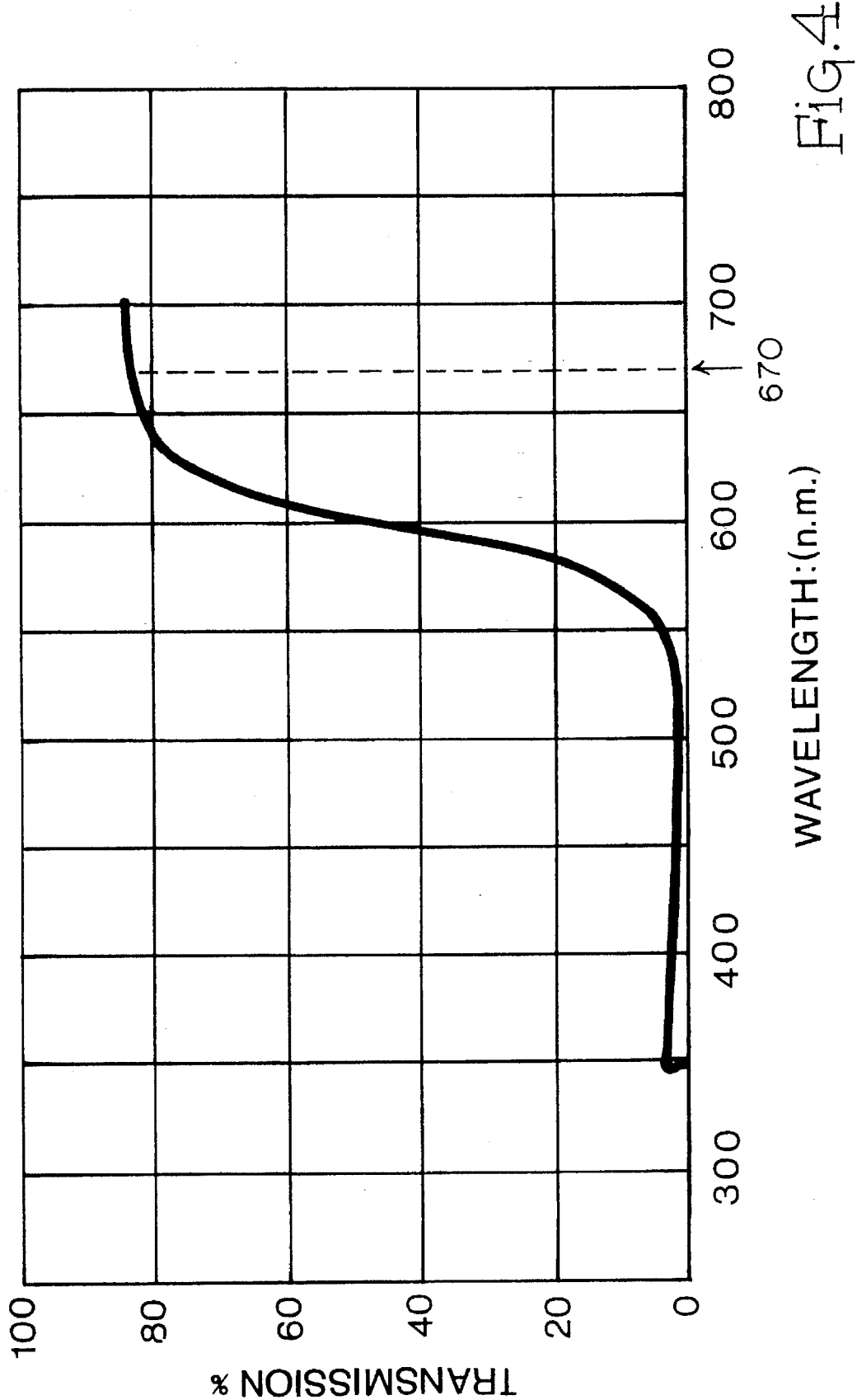
FIG. 4 is a graph showing the spectral response curve of a colored transparent window.

Because the top and bottom sheets 20, 30 and the transparent window 40 may all be formed of clear sheets of material, it is desirable to delineate the window 40 by color so that it is readily distinguishable from the remainder of the surgical drape 10. In the embodiment shown in FIG. 2, the colored ring 44 allows a user of the drape 10 to easily and quickly identify the transparent window 40 for positioning in the path of the laser beam 52. In another embodiment, the transparent window 40 itself could be made of a colored material and could function as a filter in addition to delineating the window 40 from the top and bottom sheets 20, 30. For example, a sheet of red acetate having the spectral response curve shown in FIG. 4, which allows greatest transmission of 670 nanometer wavelength light, could be used with a 670 nanometer red laser beam. Of course, other colors of windows would be used with other correspondingly colored laser beams.

The present invention may, of course, be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A surgical drape for use with an x-ray machine having a laser targeting device mounted thereon, comprising:

a) a flexible, x-ray transparent sheet material adapted to cover a portion of the x-ray machine on which the laser targeting device is mounted;

b) an opening formed in the sheet material;

c) a transparent window bonded to the sheet material and overlying the opening in the sheet material, said transparent window being made of a material which permits unimpeded transmission of a laser beam through the transparent window; and d) a colored locating means for indicating the location of said transparent window.

2. The surgical drape of claim 1 wherein the transparent window is composed of a clear acetate film bonded around its periphery to the sheet material.

3. The surgical drape of claim 2 wherein the sheet material is composed of plastic.

4. The surgical drape of claim 3 further comprising at least one tie strap attached to the sheet material for securing the surgical drape to the x-ray machine.

5. The surgical drape of claim 1 further comprising two layers of sheet material joined along a substantial portion of its periphery to form a bag open at one end.

6. The surgical glove of claim 1 wherein said colored indicating means comprises a color band surrounding said window.

7. The surgical drape of claim 1 wherein said window is colored so as to contrast with the sheet material.

8. A surgical drape adapted for use with an x-ray machine having a laser targeting device mounted thereon, comprising:

a) a flexible, x-ray transparent sheet material sized and shaped to cover a portion of the x-ray machine on which the laser targeting device is mounted;

b) an opening formed in the sheet;

c) a colored indicator surrounding the opening in the sheet material.

9. The surgical drape of claim 8 wherein the colored indicator comprises a band surrounding the opening in the sheet material.

10. The surgical drape of claim 8 wherein the band completely encircles the opening in the sheet material.

11. The surgical drape of claim 8 further including a transparent window bonded to the sheet material and overlying the opening in the sheet material, said transparent window being made of a material which permits unimpeded transmission of a laser beam through the transparent window.

12. A surgical drape adapted for use with an x-ray machine having a laser targeting device mounted thereon, comprising:

a) a flexible, x-ray transparent sheet material sized and shaped to cover a portion of the x-ray machine on which the laser targeting device is mounted;

b) an opening formed in the sheet material;

c) a transparent window bonded to the sheet material and overlying the opening in the sheet material, said transparent window being made of a material which permits unimpeded transmission of a laser beam through the transparent window; and d) wherein the transparent window is colored so as to permit transmission of light having a predetermined wavelength.

13. The surgical drape of claim 12, wherein the transparent window is composed of an acetate film.

14. The surgical drape of claim 13 wherein the window is colored so as to contrast with the sheet material.

15. The surgical drape of claim 13 wherein the acetate film has a spectral response curve that allows substantial transmission of light having a wavelength of 670 nanometers.

* * * * *